US00PP26659P2

(12) United States Plant Patent
Meinl

(10) Patent No.: US PP26,659 P2
(45) Date of Patent: Apr. 26, 2016

(54) *HYDRANGEA* PLANT NAMED 'SAXBICODAPI'

(50) Latin Name: *Hydrangea macrophylla*
Varietal Denomination: Saxbicodapi

(71) Applicant: Katrin Meinl, Dresden (DE)

(72) Inventor: Katrin Meinl, Dresden (DE)

(73) Assignee: Kühne Jungpflanzen Claus + Torsten Kühne Gbr, Dresden (DE)

( * ) Notice: Subject to any disclaimer, the term of this patent is extended or adjusted under 35 U.S.C. 154(b) by 94 days.

(21) Appl. No.: 14/120,670

(22) Filed: Jun. 14, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

U.S. PATENT DOCUMENTS

PP25,577 P3 * 5/2015 Meinl ..... Plt./250

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'Saxbicodapi', characterized by its upright and mounded plant habit; moderately vigorous to vigorous growth habit; strong stems; and large mophead-type inflorescences with red purple and green-colored sterile flowers and when treated with aluminum sulfate become darker red purple in color with development.

3 Drawing Sheets

Botanical designation: *Hydrangea macrophylla.*
Cultivar denomination: 'SAXBICODAPI'.

BACKGROUND OF THE INVENTION

The present invention relates to a new and distinct cultivar of *Hydrangea* plant, botanically known as *Hydrangea macrophylla* and hereinafter referred to by the name 'Saxbicodapi'.

The new *Hydrangea* plant is a product of a planned breeding program conducted by the Inventor in Dresden, Germany. The objective of the breeding program was to develop new container-type *Hydrangea* plants with strong stems, early flowering response and attractive leaf, stem and flower coloration.

The new *Hydrangea* plant originated from a cross-pollination in 2009 of two unidentified proprietary selections of *Hydrangea macrophylla,* not patented. The new *Hydrangea* plant was discovered and selected by the Inventor in 2011 as a flowering plant within the progeny of the stated cross-pollination in a controlled environment in Dresden, Germany.

Asexual reproduction of the new cultivar by softwood cuttings in Dresden, Germany since June, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Saxbicodapi'. These characteristics in combination distinguish 'Saxbicodapi' as a new and distinct *Hydrangea* plant:

1. Upright and mounded plant habit.
2. Moderately vigorous to vigorous growth habit.
3. Strong stems.
4. Large mophead-type inflorescences with red purple and green-colored sterile flowers and when treated with aluminum sulfate become darker red purple in color with development.

Plants of the new *Hydrangea* differ primarily from plants of the parent selections in plant habit as plants of the new *Hydrangea* are more compact than plants of the parent selections.

Plants of the new *Hydrangea* can be compared to plants of *Hydrangea macrophylla* 'Horwack', disclosed in U.S. Plant Pat. No. 25,577. Plants of the new *Hydrangea* differ primarily from plants of 'Horwack' in the following characteristics:

1. Plants of the new *Hydrangea* have stronger stems than plants of 'Horwack'.
2. Plants of the new *Hydrangea* have larger leaves than plants of 'Horwack'.
3. Plants of the new *Hydrangea* and 'Horwack' differ in sterile flower color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Saxbicodapi' grown in a container.

The photograph on the second sheet is a close-up view of a typical developing inflorescence of Saxbicodapi'.

The photograph on the third sheet is a close-up view of a typical developed inflorescence of Saxbicodapi'.

Plants used in the photographs were treated with aluminum sulfate.

DETAILED BOTANICAL DESCRIPTION

Plants used in the aforementioned photographs and in the following description were grown in 3-liter containers in a glass-covered greenhouse in Dresden, Germany and under cultural conditions typical of commercial *Hydrangea* production conditions. Plants of the new *Hydrangea* were two years old when the photographs and description were taken. During the production of the plants, day temperatures ranged from 18° C. to 25° C. and night temperatures ranged from 16° C. to 17° C. Some of the plants were treated with aluminum sulfate to "blue" the inflorescences (hereinafter referred to as "blued" plants) and some of the plants were not treated with aluminum sulfate (hereinafter referred to as non-"blued" plants). In the following description, color references are made to The Royal Horticultural Society Colour Chart, 2007 Edition, except where general terms of ordinary dictionary significance are used.

Botanical description: *Hydrangea macrophylla* 'Saxbicodapi'.

Parentage:

*Female, or seed, parent*.—Unidentified proprietary selection of *Hydrangea macrophylla,* not patented.

*Male, or pollen, parent*.—Unidentified proprietary selection of *Hydrangea macrophylla,* not patented.

Propagation:

*Type cutting*.—By softwood cuttings.

*Time to initiate roots, summer*.—About 17 days at temperatures about 18° C.

*Time to initiate roots, winter*.—About 19 days at temperatures about 18° C.

*Time to produce a rooted young plant, summer*.—About 31 days at temperatures about 18° C.

*Time to produce a rooted young plant, winter*.—About 33 days at temperatures about 18° C.

*Root description*.—Medium in thickness, fibrous; white to grey in color.

*Rooting habit*.—Moderately freely branching; medium density.

Plant description:

*Plant and growth habit*.—Perennial subshrub; upright and mounded plant habit; broadly inverted triangle; freely branching habit with about 17 lateral branches developing per plant; strong lateral branches; moderately vigorous to vigorous growth habit.

*Plant height*.—About 33.3 cm.

*Plant diameter or area of spread*.—About 52.3 cm.

*Lateral branches*.—Length: About 21.5 cm. Diameter: About 6 mm. Internode length: About 3.6 cm. Texture: Smooth, glabrous. Strength: Strong. Aspect: About 45° from vertical. Color, developing, "blued" plants: Close to 143B slightly tinged with close to N186C at the nodes. Color, developing, non-"blued" plants: Close to 143B. Color, developed, "blued" and non-"blued" plants: Close to 199C and N199C. Lenticels: Density: Moderate. Length: About 1.5 mm. Diameter: About 1 mm. Color: Close to N186C.

Leaf description:

*Arrangement*.—Opposite, simple.

*Length*.—About 11.8 cm.

*Width*.—About 9.1 cm.

*Shape*.—Ovate to broadly ovate.

*Apex*.—Broadly apiculate to cuspidate.

*Base*.—Rounded to obtuse.

*Margin*.—Serrate.

*Texture, upper and lower surfaces*.—Glabrous; slightly rugose.

*Venation pattern*.—Pinnate.

*Color*.—Developing leaves, upper surface: Slightly darker than 143A. Developing leaves, lower surface: Close to 146B. Fully expanded leaves, upper surface: Darker than between 147A and N189A; venation, close to 144A. Fully expanded leaves, lower surface: Close 147B; venation, close to 144B.

*Petioles*.—Length: About 2.5 cm. Diameter: About 4 mm. Texture, upper and lower surfaces: Smooth, glabrous. Color, upper and lower surfaces: Close to 144A.

Inflorescence & flower description:

*Flower type and habit*.—Single sterile and inconspicuous fertile flowers arranged on terminal mophead-type panicles; panicles flattened globular in overall shape; fertile flowers face mostly upright and sterile flowers face upright to outwardly.

*Fragrance*.—Faintly fragrant, pleasant.

*Natural flowering season*.—Continuous flowering from late spring to late summer in The Netherlands.

*Flower longevity, fertile flowers*.—Flowers last about one week on the plant; flowers not persistent.

*Flower longevity, sterile flowers*.—Flowers last about six weeks on the plant; flowers persistent.

*Quantity of flowers*.—Freely flowering; about 70 fertile flowers and about 160 sterile flowers per panicle.

*Panicle height*.—About 9.3 cm.

*Panicle diameter*.—About 14.8 cm.

*Flower diameter, fertile flowers*.—About 1 cm.

*Flower depth (height), fertile flowers*.—About 6 mm.

*Flower diameter, sterile flowers*.—About 3.9 cm.

*Flower depth (height), sterile flowers*.—About 8 mm.

*Flower buds, fertile flowers*.—Length: About 3 mm. Diameter: About 4 mm. Shape: Flattened globular. Color: Close to 65D; apex, close to 145B.

*Flower buds, sterile flowers*.—Length: About 9 mm. Diameter: About 8 mm. Shape: Ovoid. Color: Close to 145B.

*Petals, fertile flowers only*.—Quantity and arrangement: Five in a single whorl. Length: About 4 mm. Width: About 3 mm. Shape: Ovate, concave. Apex: Acute. Base: Cuneate. Margin: Entire. Texture, upper and lower surfaces: Smooth, glabrous. Color, "blued" plants: When opening and fully opened, upper surface: Close to 100B. When opening and fully opened, lower surface: Close to 97B; apex, close to 145C. Color, non-"blued" plants: When opening and fully opened, upper surface: Close to 62A. When opening and fully opened, lower surface: Close to 65D; apex, close to 145D.

*Sepals, fertile flowers*.—Quantity and arrangement: Five in a single whorl. Length: About 1 mm. Width: About 0.1 mm. Shape: Deltoid. Apex: Acute. Base:

Broadly cuneate. Margin: Entire. Texture, upper and lower surfaces: Smooth, glabrous. Color: When opening, upper and lower surfaces: Close to 145B to 145C. Fully opened, upper and lower surfaces: Close to 145C to 145D.

*Sepals, sterile flowers*.—Quantity and arrangement: Four in a single whorl. Length: About 2.3 cm. Width: About 2.9 cm. Shape: Broadly ovate to reniform. Apex: Bluntly acute. Base: Broadly cuneate. Margin: Serrate. Texture, upper and lower surfaces: Smooth, glabrous. Color, "blued" plants: When opening, upper surface: Close to 144B; towards the margins, close to N79C; towards the base, tinged with close to N88C to N88D. When opening, lower surface: Close to 147D; towards the margins, close to 59D; towards the base, tinged with close to N88D. Fully opened, upper surface: Close to 59C; towards the base, strongly tinged with close to N82B to N82C. With development, colors becoming closer to 63A to 63B; towards the apex, close to 59A; towards the base, close to N88A to N88B. Fully opened, lower surface: Close to 75A tinged with close to 147C. With development, colors becoming closer to 77C and towards the base, tinged with close to N88C. Color, non-"blued" plants: When opening, upper surface: Close to 144B; towards the margins, close to 53B and 60A; towards the base, close to 61D. When opening, lower surface: Close to 147D; towards the margins, close to 53C to 53D; towards the base, close to 62A to 62B. Fully opened, upper surface: Close to 58B; towards the apex, slightly tinged with close to 147C. With development, colors becoming closer to 143A to 143B; towards the margins, close to 59B; towards the base, close to 61C to 61D. Fully opened, lower surface: Close to 55B. With development, color becoming closer to 147D; toward the margins, close to 53C to 53D; towards the base, close to 62A to 62B.

*Pedicels, fertile flowers*.—Angle: About 20° from vertical. Strength: Moderately strong. Length: About 4 mm. Diameter: About 1 mm. Texture: Smooth, glabrous. Color, "blued" plants: Close to 98C. Color, non-"blued" plants: Close to 70C.

*Pedicels, sterile flowers*.—Angle: About 30° from lateral branch. Strength: Strong. Length: About 1.9 cm. Diameter: About 1.5 mm. Texture: Smooth, glabrous. Color, "blued" plants: Close to 98C. Color, non-"blued" plants: Close to 63C and marbled with close to 63B.

*Reproductive organs, fertile flowers only*.—Stamens: Quantity per flower: About eight. Filament length: About 2 mm. Filament color: Close to 65D. Anther length: About 1 mm. Anther shape: Broadly reniform. Anther color: Close to 155A. Pollen amount: Moderate to abundant. Pollen color: Close to 156D. Pistils: Pistil quantity per flower: About two or three. Pistil length: About 1.5 mm. Stigma shape: Club-shaped. Stigma color, "blued" plants: Close to 122D. Stigma color, non-"blued" plants: Close to 65C. Style length: About 1 mm. Style color, "blued" plants: Close to 122D. Style color, non-"blued" plants: Close to 65C. Ovary color: Close to 157D.

*Seeds and fruits*.—Seed and fruit development have not been observed on plants of the new *Hydrangea* to date.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Saxbicodapi' as illustrated and described.

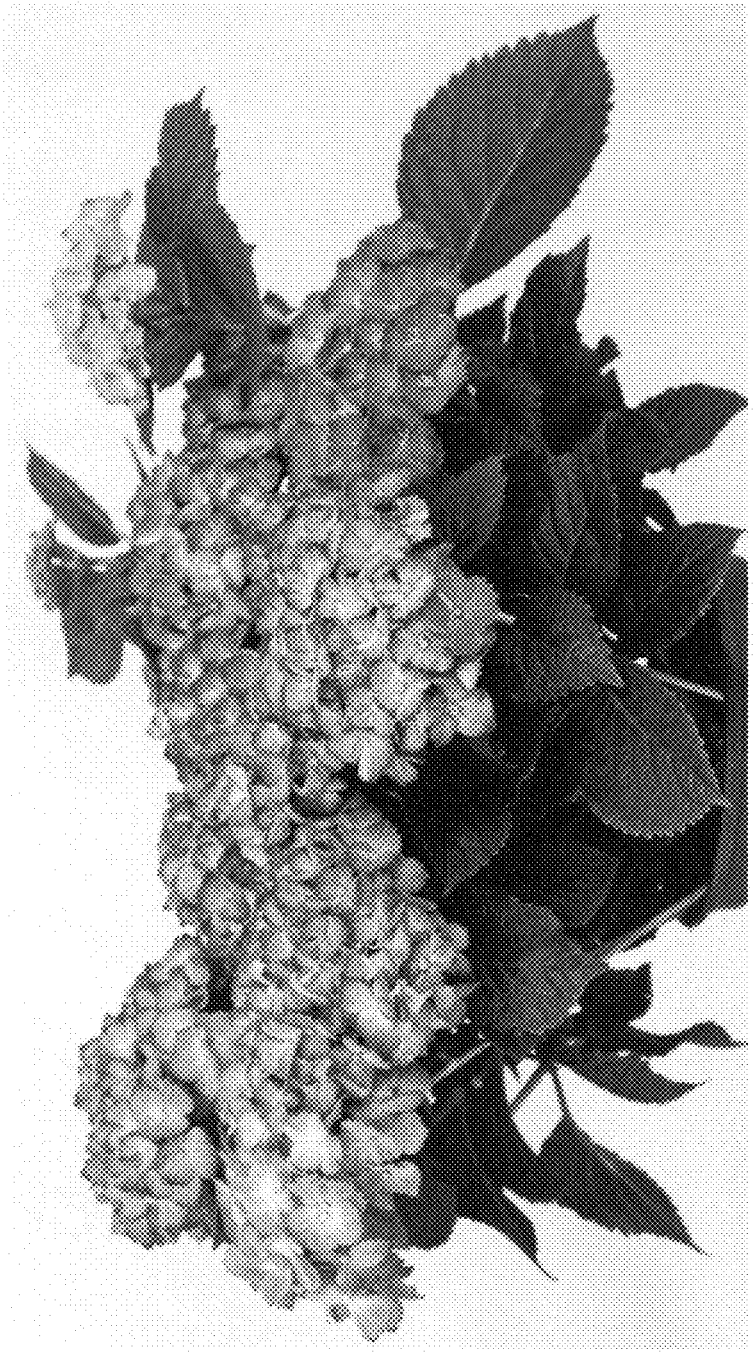

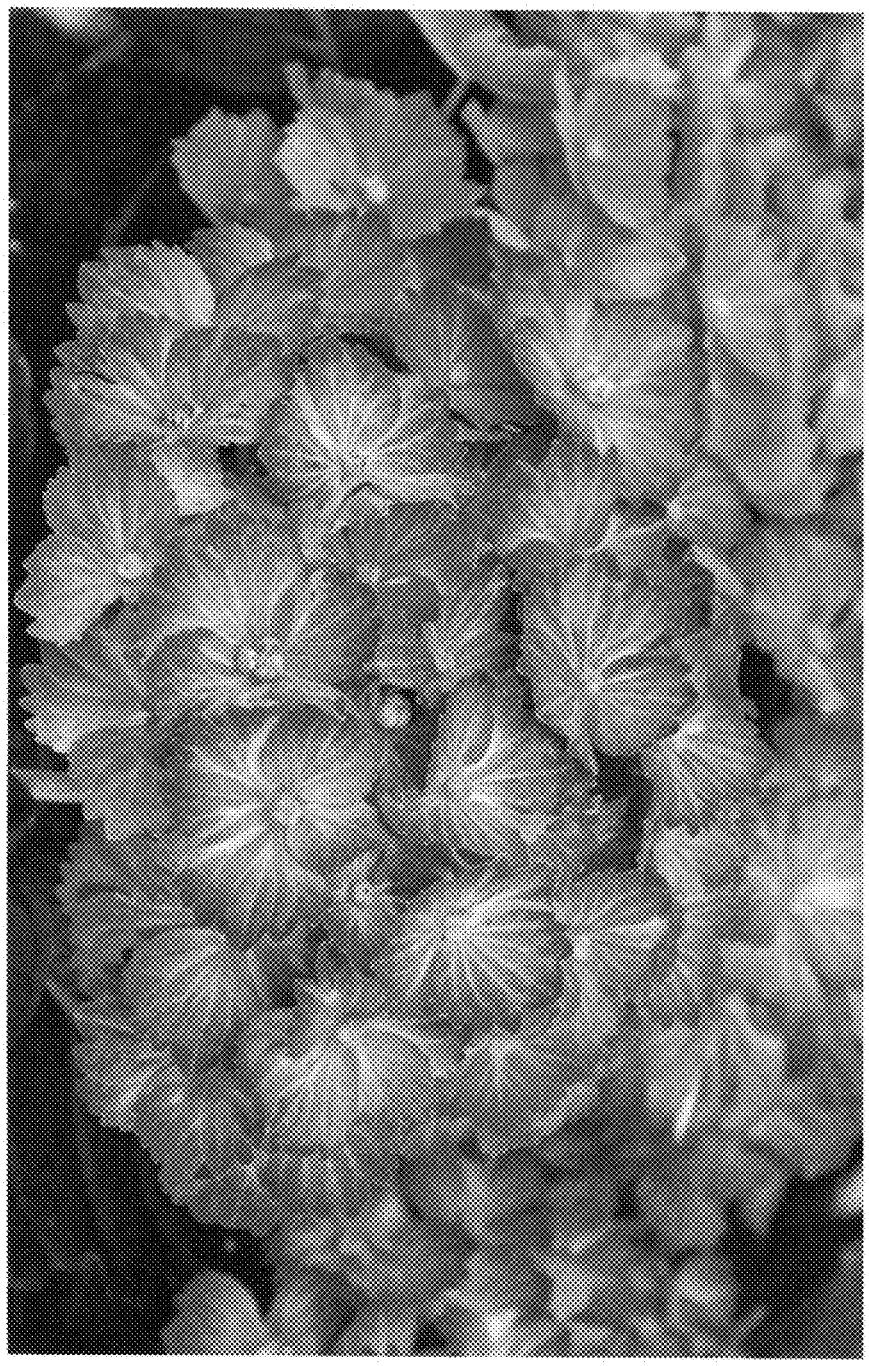

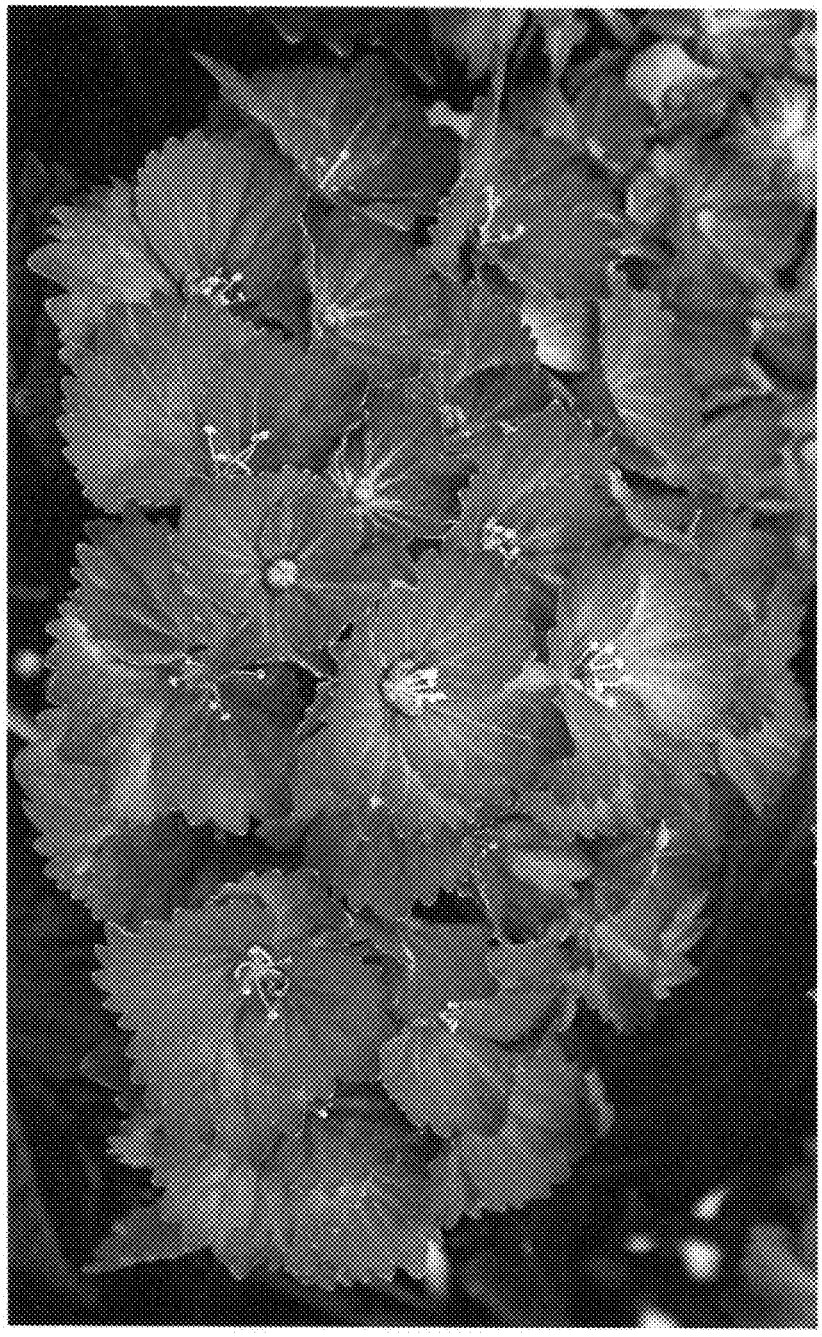

* * * * *